United States Patent
Algarni

(10) Patent No.: US 11,812,997 B2
(45) Date of Patent: Nov. 14, 2023

(54) SYSTEM AND METHOD FOR TREATING EARLY ONSET SCOLIOSIS

(71) Applicant: KING SAUD UNIVERSITY, Riyadh (SA)

(72) Inventor: Nizar Abdullah Algarni, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 18/178,478

(22) Filed: Mar. 3, 2023

(65) Prior Publication Data
US 2023/0310036 A1 Oct. 5, 2023

Related U.S. Application Data

(60) Provisional application No. 63/318,584, filed on Mar. 10, 2022.

(51) Int. Cl.
*A61B 17/70* (2006.01)

(52) U.S. Cl.
CPC ...... *A61B 17/7002* (2013.01); *A61B 17/7035* (2013.01); *A61B 17/7046* (2013.01)

(58) Field of Classification Search
CPC .... A61B 17/7014; A61B 17/7019–702; A61B 17/7025–7031; A61B 2017/681
See application file for complete search history.

(56) References Cited

U.S. PATENT DOCUMENTS

| | | | |
|---|---|---|---|
| 2005/0113831 A1* | 5/2005 | Franck | A61B 17/7052 606/246 |
| 2006/0009767 A1* | 1/2006 | Kiester | A61B 17/70 606/279 |
| 2009/0204156 A1* | 8/2009 | McClintock | A61B 17/7002 606/246 |
| 2010/0063551 A1* | 3/2010 | Richelsoph | A61B 17/7026 606/301 |
| 2010/0106192 A1* | 4/2010 | Barry | A61B 17/7014 606/264 |
| 2010/0217323 A1* | 8/2010 | Weirich | A61B 17/701 606/256 |
| 2018/0028235 A1* | 2/2018 | Simpson | A61B 17/7028 |

OTHER PUBLICATIONS

"Vertical Expandable Prosthetic Titanium Rib VEPTR™ Surgical Technique." DePuy Synthes (2016).

* cited by examiner

*Primary Examiner* — Eduardo C Robert
*Assistant Examiner* — Michelle C Eckman
(74) *Attorney, Agent, or Firm* — Nath, Goldberg & Meyer; Richard C. Litman

(57) ABSTRACT

The device for treating early onset scoliosis includes first and second tubes having first and second rods slidably disposed therein. The first tube is adapted for fixation to at least one middle vertebra of a patient's spine such that an open end thereof faces upward and a closed end thereof faces downward. The second tube is also adapted for fixation to at least one middle vertebra such that an open end thereof faces downward and a closed end thereof faces upward. A lower end of the first rod is positioned within the first tube and is resiliently biased. An upper end of the first rod is adapted for fixation to at least one upper vertebra. An upper end of the second rod is positioned within the second tube and is resiliently biased. A lower end of the second rod is adapted for fixation to at least one lower vertebra.

13 Claims, 3 Drawing Sheets

SYSTEM AND METHOD FOR TREATING EARLY ONSET SCOLIOSIS

CROSS-REFERENCE TO RELATED APPLICATION

This application claims the benefit of U.S. Provisional Patent Application No. 63/318,584, filed on Mar. 10, 2022.

BACKGROUND

1. Field

The disclosure of the present patent application relates to surgical treatments for early onset scoliosis, and particularly to a device and method for treating early onset scoliosis.

2. Description of the Related Art

Scoliosis is a condition in which a person's spine has a sideways curve. Surgery is usually recommended by orthopedists for spinal curves with a high likelihood of progression (i.e., greater than 450 to 500 of magnitude), curves that would be cosmetically unacceptable as an adult, curves in people with spina bifida and cerebral palsy that interfere with sitting and care, and curves that affect physiological functions, such as breathing. One surgical technique for treating scoliosis is the implantation of spine-based or rib-based growing rod systems. Such systems use instrumentation to attach one or two rods to the spine above and below a spinal curve. However, the use of such systems requires multiple surgeries to lengthen the rod to facilitate the child's growth. The typical lengthening protocol requires surgery every 5-6 months, thus putting the child at risk for infection and wound complications.

Magnetically controlled growing rod (MCGR) surgery is an alternative to the traditional growing rod systems. MCGR allows the rod to be lengthened without general anesthesia and surgical incision. During MCGR, the child remains awake during rod lengthening, which is accomplished using external magnets to adjust the rods. An external remote control device triggers the magnets to change the size of the rods while the child is awake in the surgeon's office. However, this method has multiple disadvantages, particularly in terms of cost and its deficiencies in correcting sagittal and coronal misalignment. Additionally, similar to traditional growing rod systems, rod lengthening must be scheduled every 5-6 months.

Growth-guided devices use instrumentation designed to correct scoliosis while allowing the child to grow. Similar to the growth rod approach, two rods are implanted on each side of the spine. With growth-guided devices, the rods are attached to screws or wires (referred to as "anchor points") along the spine. The difference between growth-guided devices and traditional growing rods or MCGR is that the spine is left to grow on its own after the initial procedure. As the child grows, the spine elongates along the rod. Using the Shilla procedure, a surgeon first performs a spinal fusion at the most severe portion of the scoliotic curve (i.e., the "apex" of the curve). The surgeon then places anchor points at the top and bottom of the curve. These points guide the rods to allow the spine to grow longer. The screws at the ends of the spine are specially designed to allow movement and growth along the rod, since the rod is not statically fixed to the spine. However, this method has the potential for breakage of the rods, thus requiring additional surgeries. Additionally, there is high risk of the need of more than two surgeries to adjust the length of the rod if the child grows more than the set length of the rod allows.

A further surgical treatment for scoliosis is vertebral body tethering (VBT), which is fusionless surgery and is appropriate for some children with progressive scoliosis. VBT involves a surgical procedure in which titanium screws are implanted into the vertebral bodies on the convex side (i.e., the outward section) of the scoliotic curve. The screws are coated with a substance that stimulates each implanted screw to fuse with the vertebral bone. A flexible strong cord designed for fusion is secured to each screw and sequentially tightened to help straighten the abnormal curve. The surgical team for VBT includes the spinal surgeon, an assistant surgeon and a thoracic surgeon. Under general anesthesia, small incisions are made at the side of the child's chest, typically via video-assisted thoracoscopic surgery (VATS). Through a small scope, a video camera is inserted into the surgical field, allowing the surgeon to see the patient's anatomy and precisely guide the instruments throughout the VBT procedure. After the surgical procedure, VBT continues to correct the scoliosis through growth modulation, i.e., the tethered side of the spine grows less that the side that is not tethered. Although promising in its results, VBT requires an extremely high level of surgical skill and expertise. In VBT, the traditional posterior approach for the spine is not used, thus requiring even experienced spinal surgeons to perform surgery using techniques that most surgeons are not familiar with, particularly involving different approaches around vital structures, such as the lungs, heart, major blood vessels, and the abdominal structure. Additionally, VBT is limited to use for curves with less than 500 of magnitude.

Thus, a device and method for treating early onset scoliosis solving the aforementioned problems is desired.

SUMMARY

The device for treating early onset scoliosis includes first and second tubes having first and second rods, respectively, slidably disposed therein. The first tube has opposed open and closed ends and is adapted for fixation to at least one middle vertebra of a patient's spine such that the open end of the first tube faces upward and the closed end of the first tube faces downward with respect to the patient's spine. The second tube similarly has opposed open and closed ends and is also adapted for fixation to at least one middle vertebra of the patient's spine such that the open end of the second tube faces downward and the closed end of the second tube faces upward with respect to the patient's spine. In an exemplary embodiment, at least a pair of middle pedicle screws may be used for fixing the first and second tubes to at least one pedicle of the at least one middle vertebra of the patient's spine. In a further exemplary embodiment, the first tube and the second tube are each fixed to the same at least one middle vertebra of the patient's spine. In another exemplary embodiment, the first tube and the second tube may each be fixed to two middle vertebrae of the patient's spine by two pedicle screws. In a further exemplary embodiment, each of the first and second tubes may be formed from cobalt chrome with an inner coating of polyethylene, such that the first and second rods are in sliding contact with the respective inner coatings of polyethylene.

The first rod has opposed upper and lower ends, the lower end being positioned within the first tube and being resiliently biased with respect to the closed end of the first tube. The upper end of the first rod is positioned external to the first tube and is adapted for fixation to at least one upper vertebra of the patient's spine. For example, at least one upper pedicle screw may be used for fixing the upper end of the first rod to at least one pedicle of the at least one upper vertebra of the patient's spine.

The second rod has opposed upper and lower ends, the upper end of the second rod being positioned within the second tube and being resiliently biased with respect to the closed end of the second tube. The lower end of the second rod is positioned external to the second tube and is adapted for fixation to at least one lower vertebra of the patient's spine. With respect to the patient's scoliotic spine, as used herein, the at least one middle vertebra is located within the vicinity of the apex of the spinal curvature. The at least one upper vertebra is located above the apex of the spinal curvature, and the at least one lower vertebra is located below the apex of spinal curvature.

In an exemplary embodiment, at least one lower pedicle screw may be used for fixing the lower end of the second rod to at least one pedicle of the at least one lower vertebra of the patient's spine. In a further exemplary embodiment, the upper end of the first rod may be fixed to two upper vertebrae of the patient's spine by a first pair of pedicle screws, and the lower end of the second rod may be fixed to two lower vertebrae of the patient's spine by a second pair of pedicle screws.

In an alternative embodiment, the device for treating early onset scoliosis includes only a single tube having opposed upper and lower open ends. The tube is adapted for fixation to at least one middle vertebra of a patient's spine such that the upper open end of the tube faces upward and the lower open end of the tube faces downward with respect to the patient's spine. A spring is centrally disposed within the tube. For example, at least one middle pedicle screw may be used for fixing the tube to at least one pedicle of the at least one middle vertebra of the patient's spine. In another exemplary embodiment, the tube may be fixed to two middle vertebrae of the patient's spine by two pedicle screws. In a further exemplary embodiment, the tube may be formed from cobalt chrome with an inner coating of polyethylene, such that the first and second rods are in sliding contact with the inner coating of polyethylene.

A lower end of a first rod is positioned within the tube, such that the lower end of the first rod contacts the spring and is resiliently biased thereby. The upper end of the first rod is positioned external to the tube, above the upper open end, and is adapted for fixation to at least one upper vertebra of the patient's spine. An upper end of a second rod is positioned within the tube, the upper end of the second rod contacting the spring such that the second rod is resiliently biased thereby. The lower end of the second rod is positioned external to the tube, below the lower open end, and is adapted for fixation to at least one lower vertebra of the patient's spine.

In an exemplary embodiment, at least one upper pedicle screw may be used for fixing the upper end of the first rod to at least one pedicle of the at least one upper vertebra of the patient's spine. In another exemplary embodiment, at least one lower pedicle screw may be used for fixing the lower end of the second rod to at least one pedicle of the at least one lower vertebra of the patient's spine. In a further exemplary embodiment, the upper end of the first rod may be fixed to two upper vertebrae of the patient's spine by a first pair of pedicle screws, and the lower end of the second rod may be fixed to two lower vertebrae of the patient's spine by a second pair of pedicle screws.

These and other features of the present subject matter will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
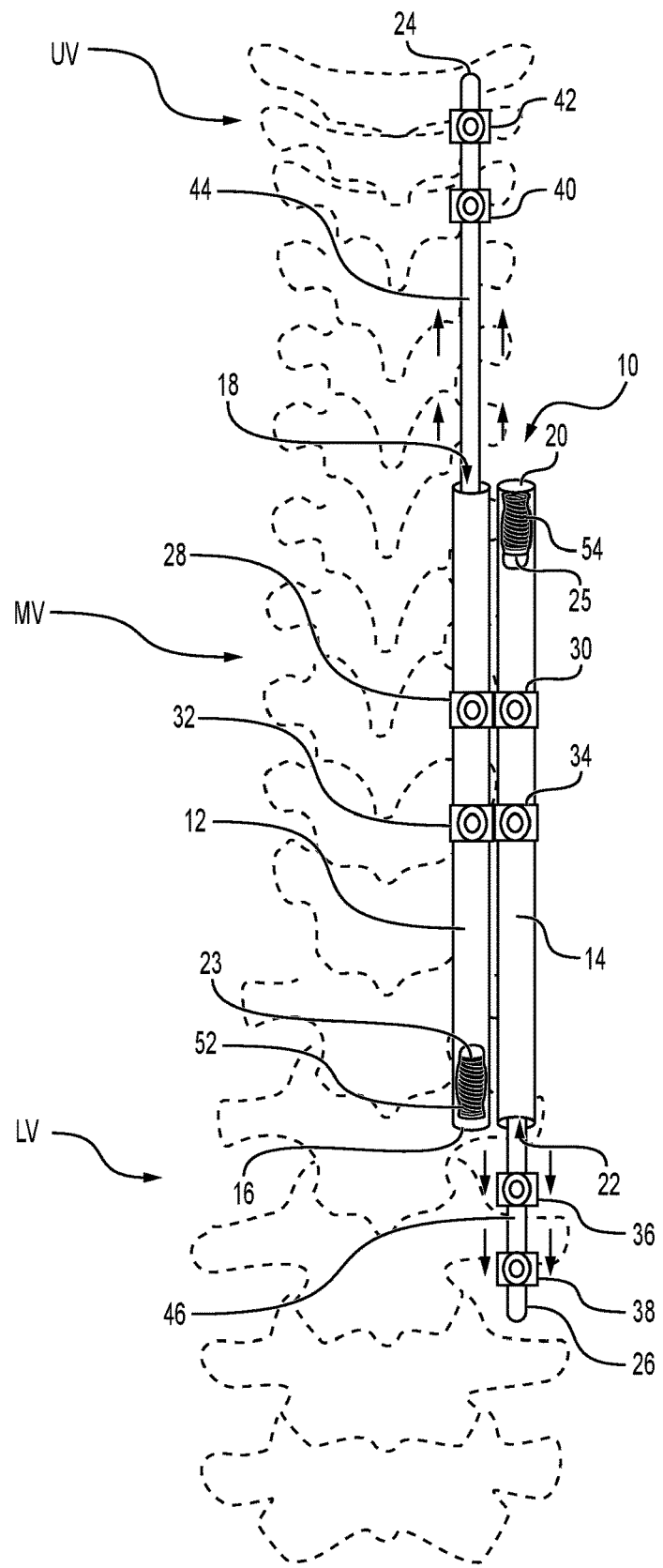
FIG. 1 is a schematic environmental, perspective view of an exemplary embodiment of a device for treating early onset scoliosis as seen from the rear of the spine, only the right side being shown for clarity, the left side being symmetrical.

As shown in FIG. 1, the device for treating early onset scoliosis 10 includes first and second tubes 12, 14, respectively, having first and second rods 44, 46, respectively, slidably disposed in the tubes 12 14. The first tube 12 has opposed closed and open ends 16, 18, respectively, and is adapted for fixation to at least one middle vertebra MV of a patient's spine, such that the open end 18 faces upward and the closed end 16 faces downward with respect to the patient's spine. The second tube 14 similarly has opposed closed and open ends 20, 22, respectively, and is also adapted for fixation to at least one middle vertebra MV of the patient's spine such that the open end 22 faces downward and the closed end 20 faces upward with respect to the patient's spine. The tubes 12, 14 may have pipe clamps or brackets connecting the tubes 12, 14 and maintaining the two tubes in parallel orientation. Although only two tubes 12, 14 on one side of the spine are shown in FIG. 1, it will be understood that in practice, the device 10 may include a symmetrical tube and rod assembly attached to the opposite side of the spine for greater stability of the spine.

In the exemplary device 10 of FIG. 1, at least a pair of middle pedicle screws may be used for fixing the first and second tubes 12, 14 to at least one pedicle of the at least one middle vertebra MV of the patient's spine. In FIG. 1, for example, the first tube 12 and the second tube 14 are each fixed to two different middle vertebrae MV of the patient's spine by two pedicle screws. In FIG. 1, the first tube 12 is fixed to the two middle vertebrae MV by pedicle screws 28, 32, and the second tube 14 is fixed to the two middle vertebrae MV by pedicle screws 30, 34. Further, as shown in FIG. 1, the first tube 12 and the second tube 14 may each be fixed to the same middle vertebrae of the patient's spine. It should, however, be understood that the first tube and the second tube 14 may be fixed to differing ones of the middle vertebrae MV.

Figure 2:
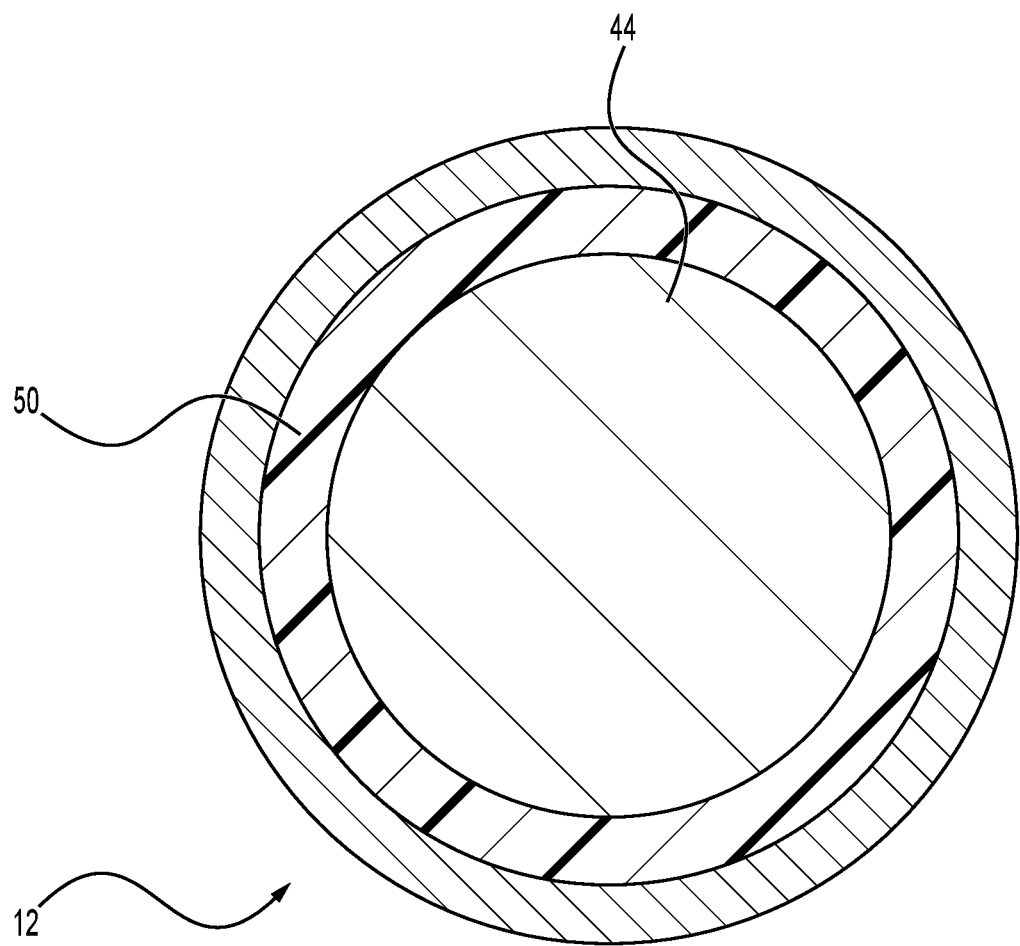
FIG. 2 is a section view through a tube of the device for treating early onset scoliosis of FIG. 1.

As shown in FIG. 2, the first tube 12 may be formed from an inert and non-bioreactive material, such as cobalt chrome or other biocompatible metal conventionally used in making prosthetic implants, with an inner coating 50 of polyethylene or the like, such that the first rod 44 is in sliding contact with the inner coating 50 of polyethylene. Alternatively, each of the tubes 12, 14 may be a cylindrical metal sleeve made of cobalt chrome or the like, having a tube made of polyethylene slidably disposed in the metal sleeve, the corresponding rods 44 and 46 being carried in the polyethylene tubes. Although FIG. 2 only shows first tube 12, it should be understood that second tube 14 may be identically constructed.

The first rod 44 has opposed lower and upper ends 23, 24, respectively, the lower end 23 being positioned within the first tube 12 and being resiliently biased with respect to the closed end 16 of the first tube 12. For example, a first helical compression spring 52 may be disposed within the first tube 12 adjacent the closed end 16, the lower end 23 of first rod 44 contacting the first spring 52 so that the first rod 44 is spring-biased in an upward direction. The upper end 24 of the first rod 44 is positioned external to the first tube 12 and is adapted for fixation to at least one upper vertebra UV of the patient's spine. At least one upper pedicle screw, for example, may be used for fixing the upper end 24 of the first rod 44 to at least one pedicle of the at least one upper vertebra UV of the patient's spine. In the particular exemplary embodiment of FIG. 1, a pair of pedicle screws 40, 42 are used to fix the upper end 24 to two different upper vertebrae UV.

The second rod 46 has opposed upper and lower ends 25, 26, respectively, the upper end 25 being positioned within the second tube 14 and being resiliently biased with respect to the closed end 20 of the second tube 14. For example, a second helical compression spring 54 may be disposed within the second tube 14 adjacent the closed end 20, the upper end 25 of the second rod 46 bearing against the second spring 54 to spring-bias the second rod 46 in a downward direction. The lower end 26 of the second rod 46 is positioned external to the second tube 14 and is adapted for fixation to at least one lower vertebra LV of the patient's spine. With respect to the patient's scoliotic spine, as used herein, the middle vertebrae MV are located within the vicinity of the apex of the spinal curvature. The upper vertebrae UV are located above the apex of the spinal curvature, and the lower vertebrae LV are located below the apex of spinal curvature.

At least one lower pedicle screw may be used for fixing the lower end 26 of the second rod 46 to at least one pedicle of the at least one lower vertebra LV of the patient's spine. In the exemplary embodiment of FIG. 1, a pair of pedicle screws 36, 38 are used to fix the lower end 26 to two different lower vertebrae LV. It should be understood that the relative dimensions of the first and second tubes 12, 14 and the first and second rods 44, 46 are shown for exemplary purposes only, and that the lengths and diameters thereof may vary depending upon the particular patient receiving treatment with the device 10.

With regard to implantation procedure, for example, the surgeon may begin the procedure by making three small incisions to respectively insert the upper pair of pedicle screws 40, 42, the middle pairs of pedicle screws 28, 30, 32, 34, and the lower pair of pedicle screws 36, 38. These pedicle screws provide the anchor points and the fusion masses which will be used to correct the deformity in the spine. On the concave side of the spinal curvature, a long straight rod (separate from first and second rods 44, 46) is inserted from the top incision and slid sub-muscularly until the rod passes through the middle incision and then the distal incision. The cantilever and bucket handle technique may be used to ensure that the rod is gradually seated well in each pedicle screw. Once the rod is seated properly, the pedicle screws may be tightened. Once the deformity in the spine is corrected to an appropriate degree using this rod, the present device for treating early onset scoliosis 10 may be applied.

The first and second rods 44, 46 are cut to optimal lengths for the patient, ensuring that the first and second rods 44, 46 will have an overlapping arrangement, similar to that shown in FIG. 1. The first and second rods 44, 46 are then respectively inserted into the first and second tubes 12, 14. The first tube 12 (with the first rod 44) is then slid from the top incision and passed sub-muscularly until it can be seen through the middle incision. The first tube 12 is then secured to the middle pedicle screws 28, 32, and the first rod 44 is pushed down in first tube 12 until optimal spring resistance can be felt. The upper end 24 of the first rod 44 is then secured to pedicle screws 40, 42. The same technique is used to insert the second tube 14 and second rod 46 through the distal incision, fixing the lower end 26 of second rod 46 to the lower pedicle screws 36, 38. Once the device for treating early onset scoliosis 10 is secured, the initial long straight rod can be removed and replaced by a second device 10 on the opposite side of the spine.

Figure 3:
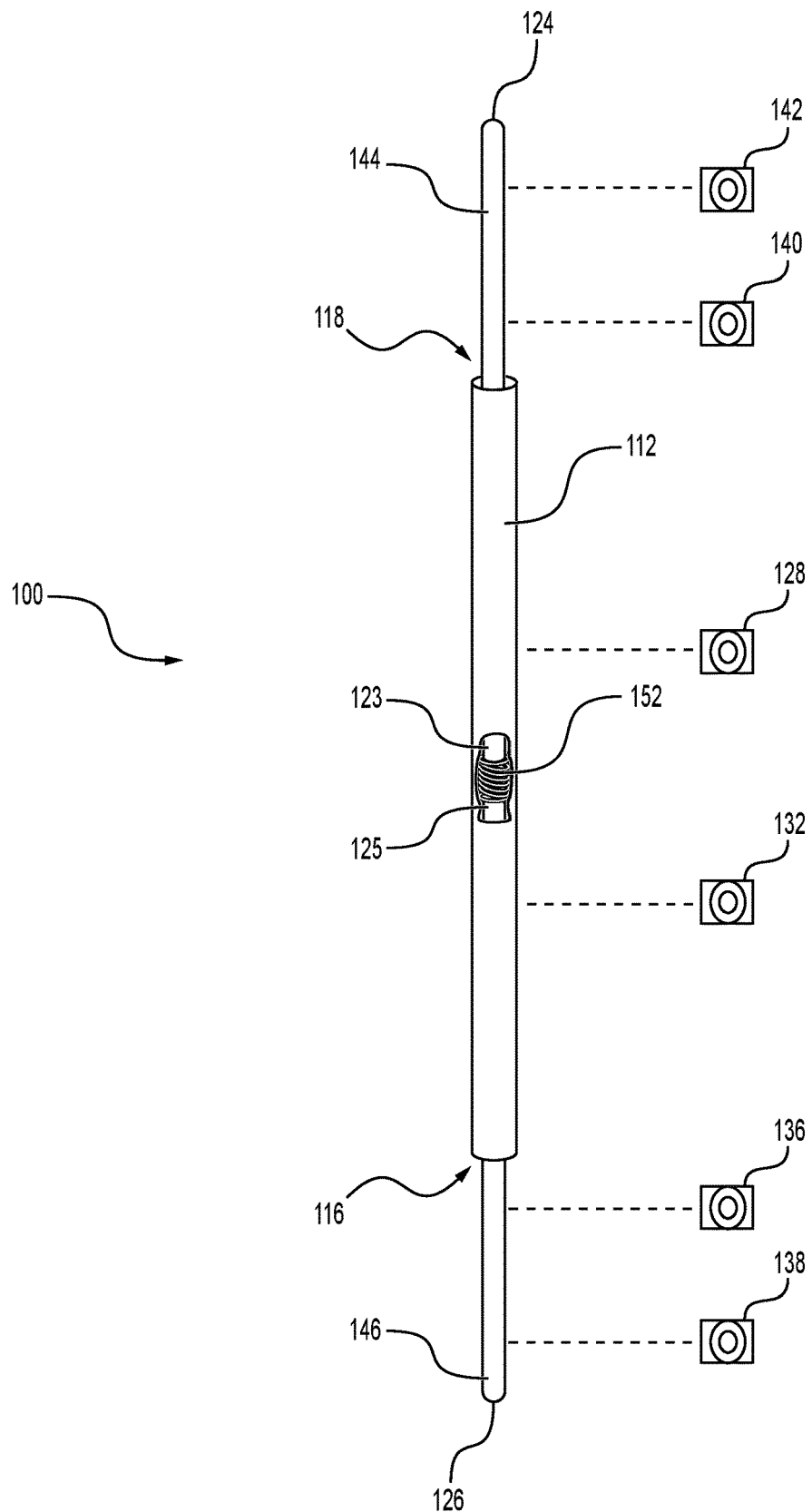
FIG. 3 is a schematic, partially exploded view of an alternative embodiment of a device for treating early onset scoliosis.

In the alternative embodiment of FIG. 3, the device for treating early onset scoliosis 100 includes only a single tube 112 on each side of the spine, the tube 112 having opposed lower and upper open ends 116, 118. The tube 112 is adapted for fixation to at least one middle vertebra of a patient's spine such that the upper open end 118 of the tube 112 faces upward and the lower open end 116 of the tube 112 faces downward with respect to the patient's spine. A helical compression spring 152 is centrally located within the tube 112. In an exemplary embodiment, at least one middle pedicle screw may be used for fixing the tube 112 to at least one pedicle of at least one middle vertebra of the patient's spine. In the particular example of FIG. 3, two such middle pedicle screws 128, 132 are provided for fixing the tube 112 to two different middle vertebrae. Similar to the previous embodiment, the tube 112 may be formed from cobalt chrome or the like with an inner coating of polyethylene or the like.

A lower end 123 of a first rod 144 is positioned within the tube 112, such that the lower end 123 contacts the spring 152 and is spring-biased thereby. The upper end 124 of the first rod 144 is positioned external to the tube 112 above the upper open end 118 and is adapted for fixation to at least one upper vertebra of the patient's spine. An upper end 125 of a second rod 146 is positioned within the tube 112, the upper end 125 of the second rod 146 bearing against the spring 152 such that the second rod 146 is spring-biased thereby. The lower end 126 of the second rod 146 is positioned external to the tube 112 below the lower open end 116 and is adapted for fixation to at least one lower vertebra of the patient's spine. In the exemplary embodiment of FIG. 3, two upper pedicle screws 140, 142 are provided for fixing the upper end 124 of first rod 144 to two different upper vertebrae, and two lower pedicle screws 136, 138 are provided for fixing the lower end 126 of second rod 146 to two different lower vertebrae.

It is to be understood that the device and method for treating early onset scoliosis is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A device for treating early onset scoliosis, comprising:
   a first tube having opposed open and closed ends, the first tube being adapted for fixation to at least one middle vertebra of a patient's spine such that the open end of the first tube faces upward and the closed end of the first tube faces downward with respect to the patient's spine;
   a first inner tube being slidably engaged within the first tube, the first inner tube having opposed open and closed ends such that the open end of the first inner tube faces upward and the closed end of the first inner tube faces downward with respect to the patient's spine;

a second tube having opposed open and closed ends, the second tube being adapted for fixation to at least one middle vertebra of the patient's spine such that the open end of the second tube faces downward and the closed end of the second tube faces upward with respect to the patient's spine;

a second inner tube being slidably engaged within the second tube, the second inner tube having opposed open and closed ends such that the open end of the second inner tube faces downward and the closed end of the first inner tube faces upward with respect to the patient's spine;

a first rod having opposed upper and lower ends, the lower end of the first rod being positioned within the first inner tube, the lower end of the first rod being resiliently biased with respect to the closed end of the first inner tube, the upper end of the first rod being positioned external to the first tube and the first inner tube and being adapted for fixation to at least one upper vertebra of the patient's spine;

a second rod having opposed upper and lower ends, the upper end of the second rod being positioned within the second inner tube, the upper end of the second rod being resiliently biased with respect to the closed end of the second inner tube, the lower end of the second rod being positioned external to the second tube and the second inner tube and being adapted for fixation to at least one lower vertebra of the patient's spine;

a first helical compression spring disposed in the closed end of said first tube to spring-bias said first rod upward by applying a force against the closed end of the first inner tube; and a second helical compression spring disposed in the closed end of said second tube to spring-bias said second rod downward by applying a force against the closed end of the second inner tube.

2. The device for treating early onset scoliosis as recited in claim 1, further comprising:
   at least one upper pedicle screw adapted for fixing the upper end of the first rod to at least one pedicle of the at least one upper vertebra of the patient's spine;
   at least one lower pedicle screw adapted for fixing the lower end of the second rod to at least one pedicle of the at least one lower vertebra of the patient's spine; and
   at least a pair of middle pedicle screws adapted for fixing the first and second tubes to at least one pedicle of the at least one middle vertebra of the patient's spine.

3. The device for treating early onset scoliosis as recited in claim 1, wherein each of the first and second tubes comprises cobalt chrome and wherein each of the first and second inner tubes comprises polyethylene.

4. The device for treating early onset scoliosis according to claim 1, further comprising at least one pipe clamp connecting said first tube with said second tube, the at least one pipe clamp maintaining said first tube and said second tube in parallel relation.

5. A method of treating early onset scoliosis, comprising the steps of:
   providing the device for treating early onset scoliosis as recited in claim 1;
   fixing the first tube of the device for treating early onset scoliosis to at least one middle vertebra of the patient's spine such that the open end of the first tube faces upward and the closed end of the first tube faces downward with respect to the patient's spine;
   fixing the second tube of the device for treating early onset scoliosis to at least one middle vertebra of the patient's spine such that the closed end of the second tube faces upward and the open end of the second tube faces downward with respect to the patient's spine;
   fixing the upper end of the first rod to at least one upper vertebra of the patient's spine; and
   fixing the lower end of the second rod to at least one lower vertebra of the patient's spine.

6. The method of treating early onset scoliosis as recited in claim 5, wherein the first tube and the second tube are each fixed to the same at least one middle vertebra of the patient's spine.

7. The method of treating early onset scoliosis as recited in claim 6, wherein the first tube and the second tube are each fixed to two middle vertebrae of the patient's spine.

8. The method of treating early onset scoliosis as recited in claim 7, wherein the first tube and the second tube are each fixed to the two middle vertebrae of the patient's spine by two pedicle screws.

9. The method of treating early onset scoliosis as recited in claim 5, wherein the upper end of the first rod is fixed to two upper vertebrae of the patient's spine, and the lower end of the second rod is fixed to two lower vertebrae of the patient's spine.

10. The method of treating early onset scoliosis as recited in claim 9, wherein the upper end of the first rod is fixed to the two upper vertebrae of the patient's spine by a first pair of pedicle screws, and the lower end of the second rod is fixed to the two lower vertebrae of the patient's spine by a second pair of pedicle screws.

11. A device for treating early onset scoliosis, comprising:
   a tube having opposed upper and lower open ends, the tube being adapted for fixation to at least one middle vertebra of a patient's spine such that the upper open end of the tube faces upward and the lower open end of the tube faces downward with respect to the patient's spine;
   a helical compression spring centrally located within the tube;
   a first rod having opposed upper and lower ends, the lower end of the first rod being positioned within the tube, the lower end of the first rod bearing against the helical compression spring such that the first rod is spring-biased upward, the upper end of the first rod being positioned external to the tube above the upper open end and adapted for fixation to at least one upper vertebra of the patient's spine; and
   a second rod having opposed upper and lower ends, the upper end of the second rod being positioned within the tube, the upper end of the second rod bearing against the helical compression spring such that the second rod is spring-biased biased downward, the lower end of the second rod being positioned external to the tube below the lower open end and adapted for fixation to at least one lower vertebra of the patient's spine.

12. The device for treating early onset scoliosis as recited in claim 11, further comprising:
   at least one upper pedicle screw adapted for fixing the upper end of the first rod to at least one pedicle of the at least one upper vertebra of the patient's spine;
   at least one lower pedicle screw adapted for fixing the lower end of the second rod to at least one pedicle of the at least one lower vertebra of the patient's spine; and at least one middle pedicle screw adapted for fixing the tube to at least one pedicle of the at least one middle vertebra of the patient's spine.

13. The device for treating early onset scoliosis as recited in claim 11, wherein the tube comprises cobalt chrome with an inner coating of polyethylene.

\* \* \* \* \*